United States Patent
McKay

(10) Patent No.: US 9,033,912 B2
(45) Date of Patent: May 19, 2015

(54) DRUG DELIVERY SYSTEM

(75) Inventor: William F. McKay, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 422 days.

(21) Appl. No.: 13/432,129

(22) Filed: Mar. 28, 2012

(65) Prior Publication Data

US 2013/0261596 A1 Oct. 3, 2013

(51) Int. Cl.
*A61M 5/31* (2006.01)
*A61M 37/00* (2006.01)
*A61M 25/01* (2006.01)

(52) U.S. Cl.
CPC .............. *A61M 5/31* (2013.01); *A61M 37/0069* (2013.01); *A61M 25/0108* (2013.01)

(58) Field of Classification Search
CPC .................................................. A61M 37/0069
USPC .......... 604/506, 57, 60–64; 606/117; 424/422
See application file for complete search history.

(56) References Cited

U.S. PATENT DOCUMENTS

| | | | |
|---|---|---|---|
| 2,513,014 A * | 6/1950 | Fields | ............................ 604/60 |
| 4,105,030 A | 8/1978 | Kercso | |
| 4,451,253 A | 5/1984 | Harman | |
| 4,576,591 A | 3/1986 | Kaye et al. | |
| 5,024,655 A | 6/1991 | Freeman et al. | |
| 5,207,678 A | 5/1993 | Harms et al. | |
| 5,212,162 A | 5/1993 | Missel et al. | |
| 5,756,127 A | 5/1998 | Grisoni et al. | |
| 6,203,813 B1 | 3/2001 | Gooberman | |
| 6,471,688 B1 | 10/2002 | Harper et al. | |
| 6,478,776 B1 | 11/2002 | Rosenman et al. | |
| 6,530,934 B1 | 3/2003 | Jacobsen et al. | |
| 6,735,475 B1 | 5/2004 | Whitehurst et al. | |
| 6,971,998 B2 | 12/2005 | Rosenman et al. | |
| 7,001,892 B1 | 2/2006 | Chmielewski et al. | |
| 7,252,651 B2 | 8/2007 | Haider et al. | |
| 8,348,883 B2 * | 1/2013 | Sklavos | ......................... 604/60 |
| 2001/0020147 A1 | 9/2001 | Staniforth et al. | |
| 2001/0043915 A1 | 11/2001 | Frey | |
| 2003/0004491 A1 | 1/2003 | Tenhuisen et al. | |
| 2004/0015133 A1 | 1/2004 | Karim | |
| 2004/0064193 A1 | 4/2004 | Evans et al. | |
| 2004/0111118 A1 | 6/2004 | Hill et al. | |
| 2004/0220545 A1 | 11/2004 | Heruth et al. | |
| 2004/0220546 A1 | 11/2004 | Heruth et al. | |

(Continued)

OTHER PUBLICATIONS

Lupron Depot Package Insert, TAP Pharmaceutical Products Inc., pp. 1-10, Mar. 28, 2012.

(Continued)

*Primary Examiner* — Laura Bouchelle
(74) *Attorney, Agent, or Firm* — Sorell Lenna & Schmidt LLP

(57) ABSTRACT

A drug delivery device for delivering a drug pellet to a site beneath the skin of a patient is provided, the drug delivery device including a housing having a chamber configured to hold at least one drug pellet, the chamber having a loading end and a delivery end, the loading end of the chamber having an opening for receiving a plunger and a drug pellet and the delivery end having an opening for receiving the plunger and passage of the drug pellet. The housing includes at least one hole substantially perpendicular to the chamber and formed to at least partially intersect the chamber. A capture pin is provided configured to be receivable within the at least one hole.

19 Claims, 4 Drawing Sheets

(56) References Cited

U.S. PATENT DOCUMENTS

| | | |
|---|---|---|
| 2004/0220547 A1 | 11/2004 | Heruth et al. |
| 2004/0220548 A1 | 11/2004 | Heruth et al. |
| 2005/0070843 A1 | 3/2005 | Gonzales |
| 2005/0074481 A1 | 4/2005 | Brekke et al. |
| 2005/0137579 A1 | 6/2005 | Heruth et al. |
| 2005/0152949 A1 | 7/2005 | Hotchkiss et al. |
| 2005/0177118 A1 | 8/2005 | Hoganson et al. |
| 2005/0245906 A1 | 11/2005 | Makower et al. |
| 2005/0249775 A1 | 11/2005 | Falotico et al. |
| 2006/0046961 A1 | 3/2006 | McKay et al. |
| 2006/0253100 A1 | 11/2006 | Burright et al. |
| 2006/0264839 A1 | 11/2006 | Veasey et al. |
| 2007/0055378 A1 | 3/2007 | Ankney et al. |
| 2007/0219564 A1 | 9/2007 | Rue et al. |
| 2008/0228193 A1 | 9/2008 | Matityahu |
| 2010/0094169 A1 * | 4/2010 | Lubock et al. ............. 600/567 |

OTHER PUBLICATIONS

Norplant Package Insert, Wyeth Pharmaceuticals Inc., pp. 1-26, Nov. 2006.

* cited by examiner

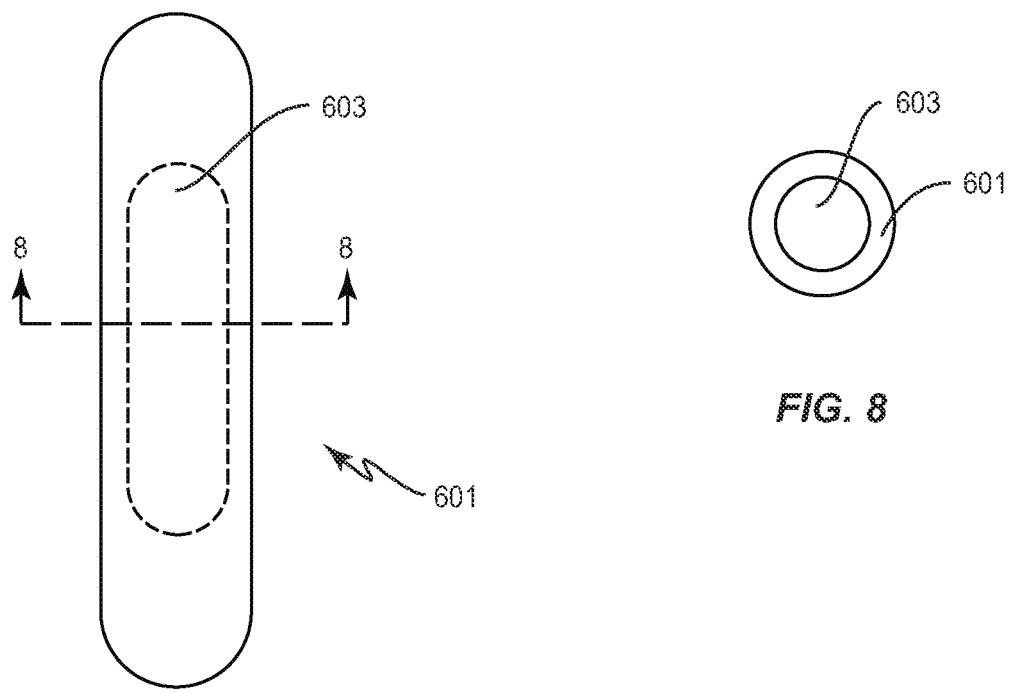
FIG. 7
FIG. 8
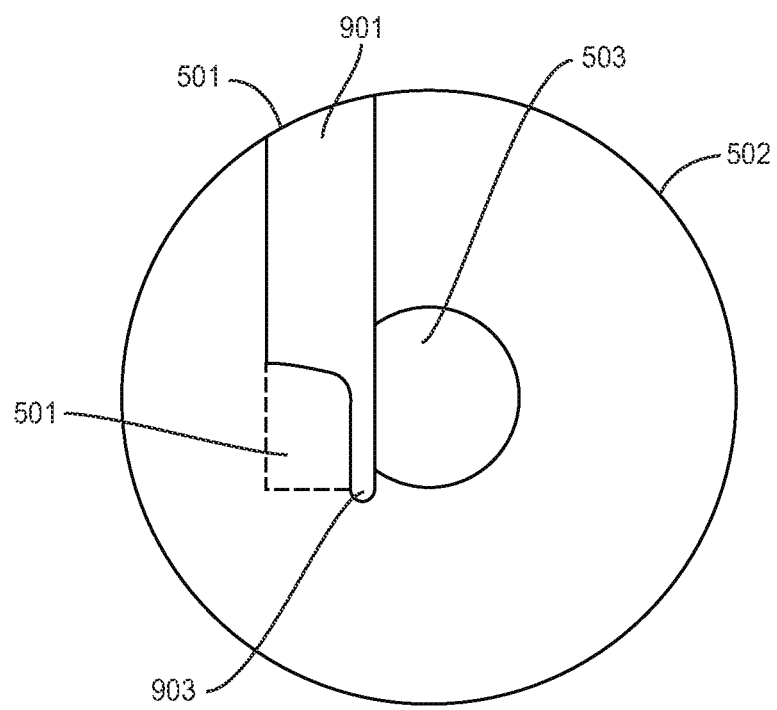
FIG. 9

DRUG DELIVERY SYSTEM

BACKGROUND

Drugs may be delivered to patients by a variety of methods including oral, intravenous, intramuscular, inhalation, topical, subcutaneous delivery or delivery directly or locally to the treatment site (e.g., intrathecally, intraspinally, intraarticularly, etc.). The method of delivery chosen depends, among other things, upon the condition being treated, desired therapeutic concentration of the drug to be achieved in the patient and the duration of drug concentration that must be maintained.

Recently, drug depots have been developed which allow a drug to be introduced or administered to sites beneath the skin of a patient so that the drug is slowly released over a long period of time. Such drug depots allow the drug to be released from the depot in a relatively uniform dose over weeks, months or even years. This method of administering drugs is becoming especially important and popular in modulating the immune, inflammation and/or pain responses in treatment of chronic conditions including rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, and the like.

Previously, drug depots and other types of implants have been inserted into the treatment site beneath the skin by use of a trocar device, which is a two-piece device that includes a cannula and an obdurator. The trocar device requires an incision to be made through the skin at the site of implant of the drug depot using a separate instrument (e.g., scalpel). A cannula and obdurator are inserted together through the skin at the incision site. Next, the obdurator is withdrawn, leaving the cannula in place as a guide for inserting the drug depot. The drug depot is inserted through the cannula, and the obdurator is used to push the implant to the end of the cannula. The cannula and obdurator are then withdrawn completely, leaving the implant in place beneath the skin.

Trocar devices are used to implant drug depots subcutaneously over a large area (e.g., 2-2.5 inches), with a typical drug depot in the order of 1½ inches long. Thus, the trocar device is not suitable for many treatment sites because it lacks precision and may cause additional trauma to the tissue surrounding the site of implant.

Other drug depot devices have been developed in an attempt to simplify implanting the drug depots. These devices have a handle for one-handed implantation of the drug depot, a needle containing the drug depot to be implanted and a rod positioned within the needle for pushing the drug depot out of the needle. Once the needle containing the drug depot has been inserted at the site of implant, a spring loaded trigger on the handle is activated which causes the needle to be automatically withdrawn by a spring leaving the implanted drug depot in place. Unfortunately, it is not possible to control the motion of the needle in these devices because the needle will automatically retract upon activation of the trigger. The complex spring loaded propelling system and trigger of these devices increase the chances that the device will jam and fail to eject the drug depot when required.

Conventional needle and syringe devices have been used to implant a drug depot to sites such as, for example, the epidural space. These devices utilize a syringe preloaded with the drug depot and an epidural needle. The needle is inserted through the skin, supraspinus ligament, intraspinus ligament, ligamentum flavum and then into the epidural space. The drug depot is delivered through the needle to the epidural space using the syringe plunger. Conventional needle and syringe devices often do not easily allow controlled and precision implant of the drug depot. If multiple drug depot implants are needed, these conventional needle and syringe devices often do not allow accurate placement of the implant in a manner so that one drug depot does not substantially interfere with the dissolution of the other.

New drug depot devices are needed, which can easily allow accurate and precise implantation of a drug depot with minimal physical and psychological trauma to a patient. When implanting several drug depots, a drug depot device is needed that is easy to operate yet accurately and precisely allows placement of each individual drug depot.

SUMMARY

New drug depot devices, which easily allow accurate and precise implantation of a drug depot with minimal physical and psychological trauma to a patient are provided. Advantageously, a drug depot device according to some embodiments greatly improves ease of use by enabling one or multiple doses of a drug to be dispensed in sequence with a minimum number of steps.

A drug depot device, in various embodiments, includes a drug cartridge comprising a housing including a chamber running longitudinally therein configured to hold one or more drug pellets. A needle may be provided connectable to the housing. The housing includes at least one capture pin hole running substantially perpendicular to a longitudinal axis of the chamber and formed to at least partially interrupt the hole. A plunger is provided configured to be insertable within the chamber. A capture pin may be provided configured to be insertable into the at least one capture pin hole, so as to partially protrude into the cylindrical travel path of the pellets, thus keeping the pellets contained within the housing. According to some embodiments, two holes are provided for insertion of two capture pins therein, to hold the pellets within the chamber and prevent them from falling out of either end of the housing. Each capture pin is designed to be deformable in at least the region where it protrudes into the chamber, so as to allow the pellets to pass through the chamber when the plunger is inserted into the chamber and a force is applied. When force is applied to the plunger, the drug pellets may be caused to deflect the capture pin and pass through the chamber and through the attached needle for insertion into a patient.

In one embodiment, a drug delivery device for delivering a drug pellet to a site beneath the skin of a patient is provided, the drug delivery device comprising a housing having a chamber configured to hold at least one drug pellet, the chamber having a loading end and a delivery end, the loading end of the chamber having an opening for receiving a plunger and a drug pellet and the delivery end having an opening for receiving the plunger and passage of the drug pellet, the housing including at least one hole substantially perpendicular to the chamber and formed to at least partially intersect the chamber, and a capture pin configured to be receivable within the at least one hole.

In another embodiment, a drug delivery device for delivering a drug pellet to a site beneath the skin of a patient is provided, the drug delivery device comprising: a housing having a chamber configured to hold at least one drug pellet, the chamber having a loading end and a delivery end, the loading end of the chamber having an opening for receiving a plunger and a drug pellet and the delivery end having an opening for receiving the plunger and passage of the drug pellet, the housing including a first hole and a second hole, each hole being substantially perpendicular to the chamber and each formed to at least partially intersect the chamber, and a capture pin configured to be receivable within each of the first and second holes.

In yet another embodiment, a method of delivering a drug pellet to a site beneath the skin is provided, the method comprising providing a housing having a chamber configured to hold at least one drug pellet, the chamber having a loading end and a delivery end, the loading end of the chamber having an opening for receiving a plunger and a drug pellet and the delivery end having an opening for receiving the plunger and passage of the drug pellet, the housing including a distal hole and a proximal hole, each hole being substantially perpendicular to the chamber and each formed to at least partially intersect the chamber; inserting a capture pin within the distal hole; loading at least one drug pellet; inserting a capture pin within the proximal hole; sterilizing the loaded housing; inserting a cannula at the target site, the cannula having a proximal end and a distal end, the proximal end of the cannula having an opening to receive a drug pellet, the distal end of the cannula capable of insertion to the site beneath the skin of the patient and having an opening for passage of the drug pellet; and attaching the loaded housing to the proximal end of the cannula, wherein movement of the plunger to an extended position moves the drug pellet out of the distal end of the chamber and moves the pellet into the proximal end and distal end of the cannula to the site beneath the skin.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIG. 7 illustrates an exemplary capture pin for use with a drug delivery device according to an aspect of the present application;

FIG. 8 illustrates a cross-sectional view taken along lines 8-8 of the capture pin of FIG. 7; and FIG. 9 illustrates an enlarged cross-sectional view taken along lines 6-6 of the drug delivery device of FIG. 5 showing a capture pin inserted within a delivery end hole according to an alternate embodiment.

Figure 1:
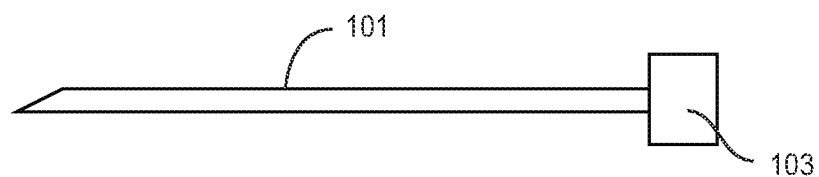
FIG. 1 illustrates an exemplary needle for use with a drug depot delivery device according to an aspect of the present application.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Reference will now be made in detail to certain embodiments of the application, examples of which are illustrated in the accompanying drawings. While the application will be described in conjunction with the illustrated embodiments, it will be understood that they are not intended to limit the application to those embodiments. On the contrary, the application is intended to cover all alternatives, modifications, and equivalents, which may be included within the application as defined by the appended claims.

The headings below are not meant to limit the disclosure in any way; embodiments under any one heading may be used in conjunction with embodiments under any other heading.

In various embodiments, a drug depot device is provided including a drug cartridge comprising a housing including a chamber formed to run longitudinally therein and configured to hold one or more drug pellets. A needle or cannula may be provided connectable to the housing via, e.g., a luer lock. In some embodiments, the housing includes at least one capture pin hole running substantially perpendicular to a longitudinal axis of the chamber, the capture pin hole being formed to at least partially interrupt the chamber. A plunger is provided configured to be slidably insertable within the chamber. A capture pin may be provided configured to be insertable into the at least one capture pin hole, so as to partially protrude into the chamber and thus interrupt the cylindrical travel path of the pellets within the longitudinal hole, thus keeping the pellets contained within the housing until they are desired to be released.

According to some embodiments, a capture pin hole is provided at each of a loading end and at a delivery end of the housing for insertion of capture pins therein, to hold the drug pellets within the chamber and prevent them from falling out of either end of the housing. According to some embodiments, each capture pin is designed to be deformable in at least the region where it intersects the chamber, so as to deflect out of the chamber to allow the drug pellets to pass through when the plunger is inserted into the chamber and a minimal force is applied. The plunger may be slidably receivable within the chamber and the needle to enable ejection of the drug pellets. The drug pellets may be caused to be ejected through the attached needle for insertion into a patient.

Figure 2:
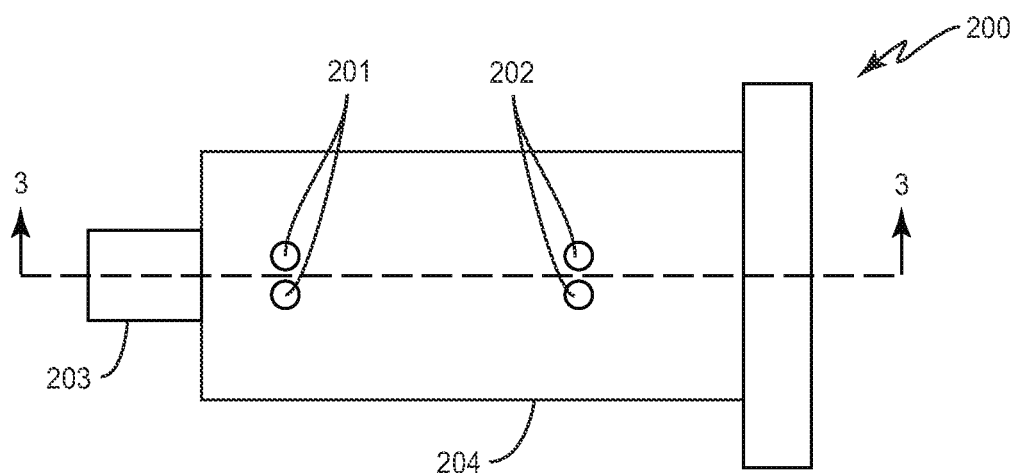
FIG. 2 illustrates a top view of an embodiment of a drug depot delivery device having a plurality of loading end holes and delivery end holes according to an aspect of the present application.
Figure 3:
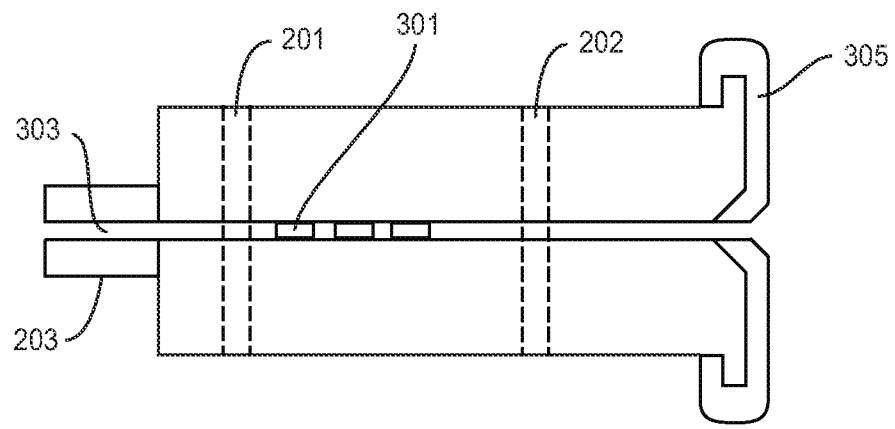
FIG. 3 illustrates a cross-sectional view taken along lines 3-3 of the drug delivery device of FIG. 2.

FIG. 2 illustrates a top view of an embodiment of a drug depot delivery device 200 having a plurality of holes 202 disposed near a loading end and a plurality of holes 201 disposed at a delivery end according to an aspect of the present application. FIG. 3 illustrates a cross-sectional view taken along lines 3-3 of the drug delivery device of FIG. 2.

Figure 4:
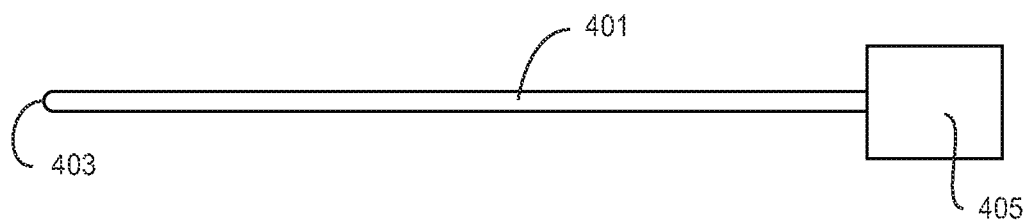
FIG. 4 illustrates an exemplary plunger for use with a drug depot delivery device according to an aspect of the present application.

FIG. 1 illustrates an exemplary needle or cannula for use with a drug depot delivery device according to an aspect of the present application. FIG. 4 illustrates an exemplary plunger for use with a drug depot delivery device according to an aspect of the present application.

According to one embodiment and referring in more detail to FIG. 1, FIG. 2, or FIG. 3, a drug depot device 200 is provided comprising a housing 204 including a chamber 303 formed to run longitudinally therein and configured to hold one or more drug pellets 301. In some embodiments, the housing 204 and/or chamber 303 may be substantially cylindrical in shape. A distal end (or delivery end) of the housing 204 may include a fastener 203 connectable to a fastener 103 of the needle 101. The fasteners 103 or 203 may comprise e.g., a luer lock or other fastening assembly for securing the needle 101 to the housing 204. A proximal (or loading end) of the housing 204 may include a cap 305 comprising, e.g., rubber material or any other suitable material to facilitate gripping of the device 200.

According to some embodiments, for example, as illustrated in FIG. 2, the housing 204 includes two pairs of capture pin holes 201, 202 each pair being substantially perpendicular to the chamber 303. The first pair of holes 202 may be provided near the loading end of the housing 204, and the second pair of holes 201 may be provided near the delivery end of the housing 204. According to some embodiments, each pair 201, 202 is formed to at least partially intersect the chamber 303, and each pair of holes 201, 202 is further configured to receive a pair of capture pins (described further with respect to FIGS. 6-9).

In some embodiments, e.g., as shown in FIG. 2, each pair of capture pin holes 201 may be formed to at least partially interrupt opposing sides of the chamber 303. This embodiment may be useful in applications where drug pellets 301 are desired to be retained within the chamber 303 more securely so as to prevent accidental release of the pellets 301 from the loading end or the delivery end of the housing 204.

A plunger 401 is provided configured to be receivable within the chamber 303 and within the needle 101. The plunger 401 may include at a distal end, a rounded tip 403 which, when inserted within the chamber 303, contacts and pushes out a drug pellet 301 disposed within. A proximal end of the plunger 401 may include a stopper 405 shaped and sized to prevent complete pass through of the plunger 401 within the chamber 303.

Figure 5:
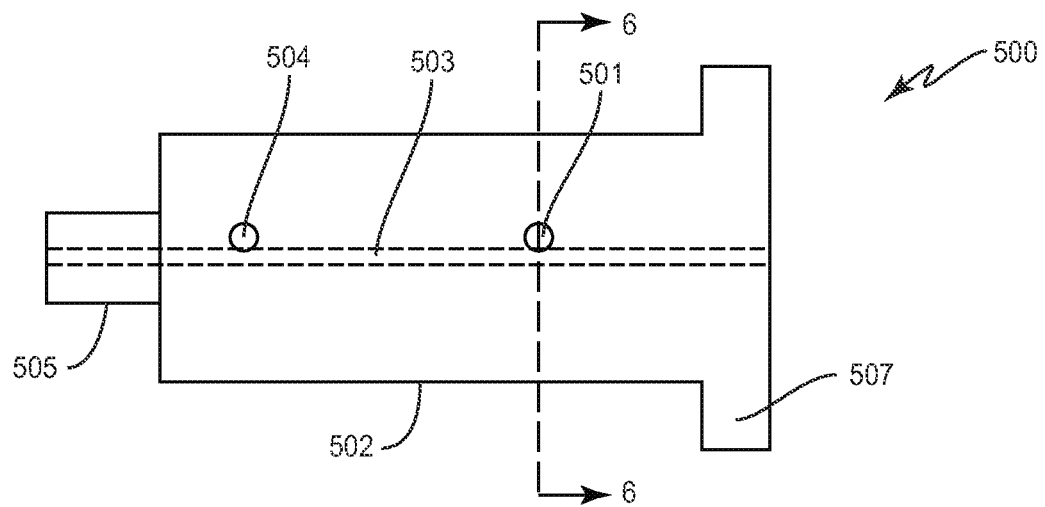
FIG. 5 illustrates a top view of another embodiment of a drug depot delivery device having a single loading end hole and a single delivery end hole according to an aspect of the present application.

FIG. 5 illustrates a top view of another embodiment of a drug depot delivery device having a single loading end hole 501 and a single delivery end hole 504 according to an aspect of the present application. According to various embodiments, an example of which is shown in FIG. 5, a drug depot device 500 is provided comprising a housing 502 including a chamber 503 formed to run longitudinally therein and configured to hold one or more drug pellets 301 of FIG. 3. In some embodiments, the housing 502 and/or chamber 503 may be substantially cylindrical in shape. A distal end (or delivery end) of the housing 502 may include a fastener 505 connectable to the fastener 103 of the needle 101 (shown in FIG. 1). The fasteners 103, 505 may comprise e.g., a luer lock or other fastening assembly for securing the needle 101 to the housing 505. A proximal (or loading end) of the housing 502 may include a cap 507 comprising, e.g., rubber material to facilitate gripping of the device 500.

Figure 6:
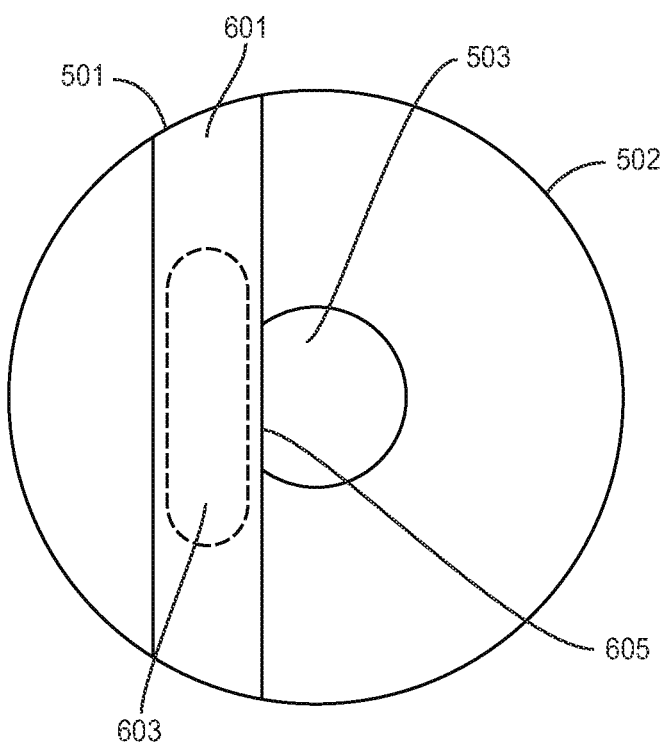
FIG. 6 illustrates an enlarged cross-sectional view taken along lines 6-6 of the drug delivery device of FIG. 5 showing a capture pin inserted within a delivery end hole according to one embodiment.

FIG. 6 illustrates an enlarged cross-sectional view taken along lines 6-6 of the drug delivery device of FIG. 5 showing a capture pin 601 inserted within the delivery end hole 501 according to one embodiment. As can be seen in the exemplary depiction of FIG. 6, the delivery end hole 501 partially intersects the chamber 503 on only one side. This enables an inserted capture pin 601 to have a region 605 which partially protrudes into one side of the chamber 503.

The partial protrusion of the inserted capture pin 601 into the chamber 503 thus impedes the cylindrical travel path of the drug pellets 301 of FIG. 3 loaded within the chamber 503, thus keeping the pellets contained within the chamber 503 until they are desired to be released. In some embodiments, e.g., as shown in FIG. 6, the delivery end hole 504 and loading end hole 501 are formed to partially interrupt the chamber 503 on one side. This may be desirable in applications where a minimal force is desired to eject the drug pellets.

In various embodiments, e.g., also as shown in FIG. 6, a single hole 501 may be provided near a loading end and a single hole 504 may be provided at a delivery end for insertion of capture pins therein, to hold the drug pellets within the chamber 503 between each of the inserted capture pins and thus prevent the pellets from falling out of either the loading or delivery end of the housing.

Each capture pin 601 is designed to be deformable in at least a region 605 where it intersects the chamber, so as to allow the drug pellets to pass through when the plunger 401 of FIG. 4 is inserted into the chamber 503 and a minimal force is applied to the plunger 401.

The capture pin 601 may be configured in various ways to be rendered readily deformable, i.e., to be enabled to be deflected out of the chamber 503 due to pressure applied by a drug pellet being forcibly ejected through the chamber 503 with a plunger 401. For example, FIG. 7 illustrates an enlarged view of an exemplary capture pin 601 for use with a drug delivery device according to an aspect of the present application. FIG. 8 illustrates a cross-sectional view taken along lines 8-8 of the capture pin 601 of FIG. 7.

In some embodiments, the pin 601 may be configured to have a hollow interior or cavity 603. This provides a thinner area in at least region 605 of the pin 601 which enables it to be more readily deformable or bendable in that region.

In some embodiments, the pin, housing and or plunger can have a marker visibly disposed thereon, to indicate the amount of pellets delivered and/or when the drug chamber is open or closed.

In various other embodiments, alternate designs of the capture pin may be contemplated to provide deformability/flexibility in at least a region in which the capture pin protrudes into the chamber 503. For example, FIG. 9 illustrates an enlarged cross-sectional view taken along lines 6-6 of the drug delivery device of FIG. 5 showing a capture pin 901 inserted within a delivery end hole 501 according to an alternate embodiment. In this exemplary embodiment, the hole 501 is provided passing only partially through the housing 502, for example, at least up to and including the diameter of the chamber 503. The capture pin 901 includes a tapered end 903 which protrudes into the chamber 503. The tapered end 903 may comprise a thinned or slivered portion having a reduced thickness. The tapered end 903 may be of any thickness to achieve the desired flexibility/deformability of the capture pin 901.

The capture pins 601, 901 may be formed of any materials, e.g., plastics, metals, composites, and may include resilient properties which will enable the pins to spring back to their original shape after any pressure causing deformation is released. Thus, in some embodiments, the capture pins may be used repeatedly for retaining and releasing drug pellets, without any reduction in effectiveness or use of the drug delivery system.

According to various embodiments, a method for assembling a drug delivery device and delivering a drug pellet to a site will now be discussed. A housing is provided having a chamber configured to hold at least one drug pellet, the chamber having a loading end and a delivery end. The loading end of the chamber has an opening for receiving a plunger and a drug pellet. The delivery end of the chamber has an opening for receiving the plunger and passage of the drug pellet. The housing includes a distal hole and a proximal hole, each of these holes being substantially perpendicular to the chamber and each formed to at least partially intersect the chamber.

The housing is prepared by inserting a capture pin within the distal hole. Any desired number of drug pellets may be loaded into the chamber. The loaded pellet(s) will be prevented from being released from the delivery end of the chamber by the inserted capture pin in the distal hole.

When the desired number of pellets is loaded in the chamber, a capture pin is inserted within the proximal hole. Thus, the loaded pellet(s) will also be prevented from be released from the loading end of the chamber by the inserted capture pin in the proximal end. Accordingly, the loaded pellet(s) will be securely retained within the chamber. The housing is then sealed, packaged and sterilized.

A cannula is inserted at a target site, such as a site beneath the skin. The cannula has a proximal end and a distal end, the proximal end of the cannula having an opening to receive a drug pellet, the distal end of the cannula capable of insertion to the site beneath the skin of the patient and having an opening for passage of the drug pellet.

The loaded housing is attached to the proximal end of the cannula via a fastening means, such as a luer lock. Movement of the plunger within the chamber to an extended position moves the drug pellet out of the distal end of the chamber and moves the pellet into the proximal end and distal end of the cannula to the site beneath the skin.

According to some embodiments, the action of pushing the plunger will cause the user to feel some resistance from the capture pins which partially intersect the chamber, in particular, when a drug pellet is being pushed past the distal capture pin, thus providing physical feedback to the user during insertion of the drug pellets. This enables the user to know how many drug pellets have been inserted. Alternate designs may be provided for providing and/or regulating physical feedback as each pellet is pushed passed the distal capture pin. For example, as shown in FIG. 2, a greater number of capture pins may be inserted into the chamber to increase the force needed to eject the pellets. Alternatively or in addition, visual markings may be provided on the plunger to indicate how many pellets have been inserted.

Advantageously, the drug delivery device according to the present application is comprised of a minimum number of moving parts, and is extremely user friendly, ultimately reducing the injection steps needed for the delivery of the drug pellets to a single injection step.

Cannula or Needle

The cannula or needle of the drug depot device is designed to cause minimal physical and psychological trauma to the patient. Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, nitinol, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The cannula or needle of the drug depot device has a diameter that is larger than the diameter of at least part of the plunger (e.g., tip, middle, etc.) to allow at least part of the plunger to be slidably received within the cannula or needle. In various embodiments, the diameter of the cannula or needle is substantially the same throughout. In other embodiments, the diameter of the needle or cannula becomes smaller approaching the distal end for drug delivery.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. Some examples of lengths of the cannula or needle may include, but are not limited to, from about 50 to 150 mm in length, for example, about 65 mm for epidural pediatric use, about 85 mm for a standard adult and about 150 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is about 14 gauge, while the smallest diameter is about 25 gauge. In various embodiments the gauge of the needle or cannula is about 17 to about 25 gauge.

In various embodiments, the plunger, cannula or drug depot include markings that indicate location at or near the site beneath the skin. Radiographic markers can be included on the drug depot to permit the user to accurately position the depot into the site of the patient. These radiographic markers will also permit the user to track movement and degradation of the depot at the site over time. In this embodiment, the user may accurately position the depot in the site using any of the numerous diagnostic-imaging procedures. Such diagnostic imaging procedures include, for example, X-ray imaging or fluoroscopy. Examples of such radiographic markers include, but are not limited to, barium, calcium phosphate, and/or metal beads.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

In various embodiments, the drug depot comprises a drug cartridge containing drug pellets loaded within the chamber of the drug cartridge, when the plunger is moved to the extended position, the drug cartridge will remain within the housing and the chamber of the drug cartridge will guide the tip of the plunger longitudinally and the drug pellet will be released from it when it is in the extended position. A subsequent or second pellet may be administered by repositioning the needle at a target site, removing the plunger so that it is at a position above the drug cartridge, and rotating the drug cartridge at a position horizontal to the plunger and cannula to align the drug chamber and drug depot with the cannula and plunger. The plunger is then slid in a vertical direction within the housing to release the drug depot from the chamber into the cannula where the drug depot can be delivered to the target site by pushing it out the tip of the needle using the plunger. In this way, sequential delivery of a drug can be accomplished. Thus, the above procedure (e.g., repositioning the needle, removing the plunger, rotating the drug cartridge, inserting the plunger, delivering the drug depot) can be repeated multiple times to deliver multiple drug depots to the target tissue site.

In various embodiments, surrounding the opening of the proximal end of the cannula or needle is a generally cylindrical hub having an engagement means (shown as internal threading) for engaging the housing. Engagement means include, but are not limited to, threading, tracks, clips, ribs, projections, and the like that allow a secure connection between the housing and the proximal end of the cannula. For example, in various embodiments the engagement means may be a luer lock connection, where the cannula has mating threads that mate with the threads disposed on or in the housing.

Housing

The housing may be of various shapes including, but not limited to, cylindrical or round such that the housing allows for the affixation to the cannula as well as the drug cartridge and the plunger.

The housing may comprise a variety of materials, such as, for example, polyurethane, polyurea, polyether(amide), PEBA, thermoplastic elastomeric olefin, copolyester, and styrenic thermoplastic elastomer, steel, nitinol, aluminum, stainless steel, titanium, metal alloys with high non-ferrous metal content and a low relative proportion of iron, carbon fiber, glass fiber, plastics, ceramics or combinations thereof.

Like the cannula or needle, in various embodiments, the housing may have dose indicator markings (e.g., numbers, lines, letters, radiographic markers, etc.) to indicate the number of drug depots delivered. In various embodiments, the plunger includes markings that indicate location at or near the site beneath the skin.

The housing may have contours and allow easy grasping of the device during use for insertion of the drug depot. The housing can be angled for right and left hand users or can be generic for both hands. In various embodiments, the housing can comprise an upper opening, a middle opening, and a lower opening. The upper, middle and lower openings allow a plunger to slide through the openings. The middle opening of the housing, in various embodiments, will receive the drug cartridge and the user can align the chamber of the drug cartridge with the upper middle and lower openings so that the plunger can pass through and deliver the drug depot.

Plunger

Although the first end of the plunger is shown as a knob, it will be understood that the knob can be a top, dial, cap, handle or any member that allows the user to utilize the plunger. The plunger has a second end that includes a tip, which is capable of moving the drug depot within the cannula. In other embodiments, the tip of the plunger is sufficiently pointed so that it is capable of insertion to the site beneath the skin of the patient and the cannula or needle is blunted and used to guide the drug depot to the site.

The plunger has a diameter less than the cannula or needle so that it can be slidably received therein. The plunger may be longer, the same size, or smaller in length than the cannula or needle. In embodiments where the plunger extends from the distal end of the cannula or needle, the plunger is usually longer than the cannula or needle. In some embodiments, the tip of the plunger can be sharp or blunt. The sharper tip of the plunger can be used in embodiments where the drug cartridge has superior and inferior covers that the sharp tip of the plunger can pierce.

The plunger may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof. The plunger may optionally include one or more tapered regions.

Like the cannula or needle, in various embodiments, the plunger may have dose indicator markings (e.g., numbers, lines, letters, radiographic markers, etc.) to indicate the number of drug depots delivered. In various embodiments, the plunger includes markings that indicate location at or near the site beneath the skin.

The plunger tip, which may be a complementary shape to the drug pellet, allows the plunger tip to snuggly fit within the end of the drug pellet for easier drug delivery. The drug pellet may have a rounded end for easier insertion at the desired site.

Drug Depot

In various embodiments, the device comprises a drug depot. A drug depot comprises a physical structure to facilitate implantation and retention in a desired site (e.g., a synovial joint, a disc space, a spinal canal, a tissue of the patient, etc.). The drug depot also comprises the drug. The term "drug" as used herein is generally meant to refer to any substance that alters the physiology of the patient. The term "drug" may be used interchangeably herein with the terms "therapeutic agent", "therapeutically effective amount", and "active pharmaceutical ingredient". It will be understood that a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 1 mm to about 5 cm from the implant site.

Examples of drugs suitable for use in the drug depot, include, but are not limited to an anti-inflammatory agent, analgesic agent, or osteoinductive growth factor or a combination thereof. Anti-inflammatory agents include, but are not limited to, salicylates, diflunisal, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine [2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone, protein inhibitors of TNF, such as etanercept, Remicade, IL-1, such as Kineret®, p38, RANK, RANKL or a combination thereof.

Suitable osteoinductive factors include, but are not limited to, a bone morphogenetic protein, a growth differentiation factor, a LIM mineralization protein or a combination thereof.

Suitable analgesic agents include, but are not limited to, acetaminophen, lidocaine, bupivicaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papavereturn, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof. Analgesics also include agents with analgesic properties, such as for example, amitriptyline, carbamazepine, gabapentin, pregabalin, clonidine, or a combination thereof.

A "depot" includes but is not limited to capsules, microspheres, particles, coating, matrices, wafers, pills, pellets or other pharmaceutical delivery compositions. In various embodiments, the depot may comprise a bioerodible, a bioabsorbable, and/or a biodegradable biopolymer that may provide immediate release, or sustained release of the drug. Examples of suitable sustained release biopolymers include but are not limited to poly(alpha-hydroxy acids), poly(lactide-co-glycolide) (PLGA), polylactide (PLA), polyglycolide (PG), polyethylene glycol (PEG) conjugates of poly(alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations. In various embodiments, the drug depot comprises poly(lactide-co-glycolide) (PLGA), polylactide (PLA), polyglycolide (PGA), D-lactide, D,L-lactide, L-lactide, D,L-lactide-ε-caprolactone, D,L-lactide-glycolide-ε-caprolactone or a combination thereof.

In various embodiments, the drug depot comprises drug pellets loaded with a therapeutically effective amount of the therapeutic agent, wherein the pellets are injected into a synovial joint, a disc space, a spinal canal, or a soft tissue surrounding the spinal canal. In various embodiments, the drug pellets comprise a gel in viscous form and microspheres loaded with a therapeutic agent, wherein the combination of gel and microspheres are positioned into a synovial joint, disc space, a spinal canal, or a soft tissue surrounding the spinal canal of a subject.

A "therapeutically effective amount" is such that when administered, the drug results in alteration of the biological activity, such as, for example, inhibition of inflammation, reduction or alleviation of pain, improvement in the condition, etc. The dosage administered to a patient can be as single or multiple doses depending upon a variety of factors, including the drug's pharmacokinetic properties, the route of administration, patient conditions and characteristics (sex, age, body weight, health, size, etc.), extent of symptoms, concurrent treatments, frequency of treatment and the effect desired.

In one exemplary embodiment, the drug depot is in the form of a pellet. The pellet can be any shape, such as for example, bullet shaped, spherical, substantially spherical, flaked, rod shaped, square, oval, etc. In various embodiments, an aspect ratio (a ratio of the length of the pellet divided by the width found at an angle of 90° in respect to the length) which is less than about 1.4 to about 1.05. The proximal end of the drug pellet may allow the plunger tip to snuggly fit within the proximal end of the drug pellet for easier drug delivery. The distal end of the drug pellet may be rounded for easier insertion at the site.

In various embodiments, the drug pellet comprises a bullet-shaped body that is made from a biodegradable material. In alternative embodiments, the body of the pellet may be made from a non-biodegradable material. A non-biodegradable body could be a porous hollow chamber filled with the therapeutic agent alone or incorporated into a degradable polymer. It may be desirable to make the body non-degradable to be able to retrieve it after it has released its contents. Non-limiting examples of suitable biodegradable materials for the pellet body include polyorthoesters (POE), polylacticglycolic acid (PLGA) polysacharides (Saber technology), polycapralactone, polyfumarate, tyrosine polycarbonate, etc. The body may be solid, and the therapeutic agent may be dispersed throughout the material that forms the body. The dispersal of the therapeutic agent may be even throughout the body. Alternatively, the concentration of the therapeutic agent may vary throughout the body. As the biodegradable material of the body degrades at the site, the therapeutic agent is released.

Procedures for making pellets include, but are not limited to, extrusion-spheroidization, for spherical pellets where the active pharmaceutical ingredient (API) and any inactive ingredients (excipients, binders, etc.) are pre-mixed, then wetted with water, in a high shear mixer to form a damp mass. The damp mass is then transferred into an extruder where it is forced through a screen or die plate, where it forms an essentially solid, cylindrical extrudate of uniform shape and size. The size of the opening in the screen or die dictate resultant pellet size. The extrudate is fed onto a rotating disk, which may be smooth or may contain a grid (waffled, grooved, etc.) and the extrudate breaks into small cylinders, which in time are rounded into spherically shaped solids. Subsequently, the pellets are dried to the desired residual moisture content, in a fluid bed dryer. Any oversized or undersized product is removed by sieving, and the resulting pellets have a narrow size distribution.

In various embodiments, the API is layered on the solid core of the pellet by solution or suspension layering or powder layering techniques. In solution or suspension layering, an API and any inactive ingredients (excipients, binders, etc.) are suspended or dissolved in water or an organic solvent. The resulting liquid is sprayed onto the outside of a core particle, which may include, for example, non-pareil sugar seed (sugar sphere), microcrystalline cellulose pellets and the like, to make the pellet having the desired potency. Solution or suspension layering may be conducted using a wide variety of process techniques, for example, by fluidized bed, Wurster bottom spray techniques, or the like. When the desired potency has been achieved, pellets are dried to the desired residual moisture content. Any oversized or undersized product may be removed by sieving, and the resulting pellets are narrow in size distribution.

Powder layering may also be used to make the drug pellets. Powdered layering involves the application of a dry powder to the pellet core material. The powder may contain the drug, or may include excipients such as a binder, flow aid, inert filler, and the like. In the powder layering technique a pharmaceutically acceptable liquid, which may be water, organic solvent, with or without a binder and/or excipients, is applied to the core material while applying the dry powder until the desired potency is achieved. When the desired potency has been achieved, the pellets may be seal coated to improve their strength, and are then dried to the desired moisture content. Any oversized or undersized product is removed by sieving, and the resulting pellets are narrow in size distribution.

In one embodiment, the pellet is made using a core of biodegradable material, such as, for example, polyglactin, polylactone, polylactide, etc. The core is then coated with a thin layer of the API, such as an anti-inflammatory agent, analgesic agent, etc. by solution, suspension, or powdered layering until the desired potency is achieved.

In various embodiments, the drug pellets can be different sizes, for example, from about 1 mm to 5 mm and have a diameter of from about 0.01 to about 2 mm. The layer or layers will each have a layer thickness of from about 0.005 to 1.0 mm, such as, for example, from 0.05 to 0.75 mm. The drug depot chambers are often larger than the drug depot dimensions to keep the drug depot within the drug chamber.

Like the cannula, needle, or plunger, in various embodiments, the drug depot (e.g., pellet, cartridge, etc.) may have dose indicator markings (e.g., numbers, lines, letters, radiographic markers, etc.) to indicate the number of drug depots delivered. In various embodiments, radiopaque marks are positioned on the depot at opposite ends of the depot to assist in determining the position of the depot relative to the treatment site. For example, the radiopaque marker could be a spherical shape or a ring around the depot.

Bulking Agent

In various embodiments, the drug depots are secured in the drug cartridge by use of a bulking agent. The bulking agent may be added to the drug depot to ensure the drug depot is secure within the chamber, such that the drug depot is released when the plunger is engaged to dislodge the drug depot from the cartridge. In some embodiments, the bulking agent is added to the drug chamber before the drug depot is added to the chamber. In some embodiments, the drug depot is added to the drug chamber first and then the drug depot is added to the chamber. In other embodiments, the bulking agent and the drug depot are added to the drug chamber together.

In some embodiments, the bulking agent can be penetrated and can be cored by the plunger and/or depot in order to release the drug depot. A bulking agent includes an excipient, which provides bulk and structure to the drug depot and holds the drug depot in position within the chamber. In some embodiments, the bulking agent prevents unwanted movement, contaminants (e.g., moisture), and breakage of the drug depot. In some embodiments, the bulking agent fills the space within the chamber so that there is little or no repositioning of the drug depot during delivery. Examples of suitable bulking agents include hydrophilic excipients, such as, water soluble polymers; sugars, such as mannitol, sorbitol, xylitol, glucitol, ducitol, inositiol, arabinitol, arabitol, galactitol, iditol, allitol, maltitol, fructose, sorbose, glucose, xylose, trehalose, allose, dextrose, altrose, lactose, talc, zinc oxide, starch, hydroxyethylstarch (hetastarch), cellulose, cyclodextrins, glycine, fructose, gulose, idose, galactose, talose, ribose, arabinose, raffinose, xylose, lyxose, sucrose, maltose, lactose, lactulose, fucose, rhamnose, melezitose, maltotriose, raffinose, altritol, their optically active forms (D- or L-forms) as well as the corresponding racemates; inorganic salts, both mineral and/or mineral organic, such as, calcium salts, such as the lactate, gluconate, glycerylphosphate, citrate, phosphate monobasic and dibasic, succinate, sulfate and tartrate, as well as the same salts of aluminum and magnesium; carbohydrates, such as, the conventional mono- and di-saccharides as well as the corresponding polyhydric alcohols; proteins, such as, albumin; amino acids, such as glycine; emulsifiable fats or polyvinylpyrrolidone or a combination thereof. Exemplary bulking agents include glycine, mannitol, dextran, dextrose, lactose, sucrose, polyvinylpyrrolidone, trehalose, glucose, wax, agar, agarose, gel-vitamin or combinations thereof. The bulking agent may be in solid, semisolid, or liquid form. In various embodiments, the bulking agent is in a powdered form.

In some embodiments, the particle size of the solid or semi-solid bulking agents range is greater than 10 microns as particles of this size are easily removed by macrophages and other cells of the immune system. In some embodiments, the bulking agent has a particle size from about 10 microns to about 1500 microns in diameter, or from about 150 microns to about 1100 microns in diameter, or from about 500 microns to about 900 microns in diameter. The size of the particles chosen for a particular application will be determined by a number of factors. Smaller particles are easier to inject with a smaller gauge size needle. The size of the particles used in a particular procedure will include consideration of the procedure employed, disease progression, the degree of degradation of the affected region, patient size, the disposition of the patient, and the preferences and techniques of the doctor performing the procedure.

In some embodiments, the bulking agent does not contain a therapeutic agent. In other embodiments, a therapeutic agent may be dispersed throughout the bulking agent and provide immediate release of the therapeutic agent.

In some embodiments, the bulking agent includes a bioerodible, a bioabsorbable, and/or a biodegradable biopolymer like the depot and/or superior and/or inferior covers. Examples of suitable materials include but are not limited to poly(alpha-hydroxy acids), poly(lactide-co-glycolide) (PLGA), polylactide (PLA), polyglycolide (PG), polyethylene glycol (PEG) conjugates of poly(alpha-hydroxy acids), mPEG, poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, ε-caprolactone, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. In various embodiments, the bulking agent comprises poly(lactide-co-glycolide) (PLGA), polylactide (PLA), polyglycolide (PGA), D-lactide, D,L-lactide, L-lactide, D,L-lactide-ε-caprolactone, D,L-lactide-glycolide-ε-caprolactone or a combination thereof.

The bulking agent can be disposed anywhere around the drug depot. For example, the bulking agent can be disposed in at least a portion of each chamber (e.g., distal end opening, proximal end opening, middle or throughout the drug chamber) so as to hold the drug pellet within the chamber. In some embodiments, the bulking agent holds the drug pellet in position and prevents unwanted movement, contaminants (e.g., moisture), and breakage of the drug pellet. The bulking agent fills the space within the chamber so that there is little or no repositioning of the pellet during drug delivery.

Sterilization

The drug device components (e.g., cannula or needle, plunger, housing, engagement means, etc.) may be lightweight, disposable and sterilizable such that when the device is assembled (e.g., the drug cartridge is attached to the housing), the weight of the device does not substantially increase. In various embodiments, one or more components of the device are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, the drug cartridge provides the advantages of ease of manufacturing in the terminal sterilization process. If the drug pellets are preloaded in the manufacturing process, gamma radiation may be required at higher doses to sterilize the drug depot loaded in the cannula or needle. This is particularly so when the cannula or needle is made from steel or metal. Thus, to sterilize the loaded depot, the dose of gamma rays must be high enough to penetrate the metal, which may destroy the API in the drug depot. By providing a drug cartridge, for example, made of plastic, the drug cartridge and drug pellets in the cartridge can be sterilized, without destroying the API and then subsequently loaded by the manufacturer or the user (e.g., surgeon, physician, nurse, etc.). Further, loading the drug depot into the drug chamber or cannula is easier. This is particularly so when dealing with multi-dose drug pellets that are relatively small (e.g., 1 mm to 5 mm), the user cannot grasp these small pellets and load them into the device. By providing them in a drug cartridge, the user does not have to substantially manipulate the individual drug pellets and the risk of contaminating the pellets particularly with sterilized pellets is reduced.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot includes a gelatin capsule.

Other methods may also be used to sterilize one or more components of the device, including, but not limited to, gas sterilization, such as, for example, with ethylene oxide or steam sterilization.

In some embodiments, the housing, drug cartridge, and/or cannula are transparent so the user can see the position of the plunger and/or the drug depot in the chamber of the drug cartridge. Thus, indicator markings, in this embodiment, are not needed.

In various embodiments, a kit is provided for delivering a drug pellet to a site beneath the skin of a patient, the kit comprising: a sterilized drug delivery device, comprising: a cannula having a proximal end and a distal end, the proximal end of the cannula having an opening to receive the drug pellet, the distal end of the cannula capable of insertion to the site beneath the skin of the patient and having an opening for passage of the drug pellet; a housing having a chamber configured to hold at least one drug pellet, the chamber having a loading end and a delivery end, the loading end of the chamber having an opening for receiving a plunger and a drug pellet and the delivery end having an opening for receiving the plunger and passage of the drug pellet, the housing including at least one hole substantially perpendicular to the chamber and formed to at least partially intersect the chamber; and a capture pin configured to be receivable within the at least one hole.

In various embodiments, a kit is provided which may include additional parts along with the drug depot device combined together to be used to implant the drug depot. The kit may include the drug depot device in a first compartment. The second compartment may include the drug cartridge, and any other instruments needed for the implant. A third compartment may include gloves, drapes, wound dressings and other procedural supplies for maintaining sterility of the implanting process, as well as an instruction booklet. A fourth compartment may include additional cannulas and/or needles. Each tool may be separately packaged in a plastic pouch that is radiation sterilized. A cover of the kit may include illustrations of the implanting procedure and a clear plastic cover may be placed over the compartments to maintain sterility.

In various embodiments, the seal between the plunger tip and the cannula or needle can be air tight so that when the cannula or plunger penetrates the skin, at times, fluid (e.g., blood, spinal fluid, synovial fluid, etc.) may be drawn up into the cannula or needle. This fluid will be expelled when the plunger is re-inserted into the cannula or needle and the drug depot is released.

The device may be used for localized and/or targeted delivery of the drug to a patient to treat a disease or condition such as for example, rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, bone muscles, and the like.

In various embodiments, the drug depot device is used to treat pain, or other diseases or conditions of the patient. Pain includes acute pain and neuropathic pain. Acute pain refers to pain experienced when tissue is being damaged or is damaged (e.g., injury, infection, etc.). As contrasted to acute pain, neuropathic pain serves no beneficial purpose. Neuropathic pain results when pain associated with an injury or infection continues in an area once the injury or infection has resolved. Sciatica provides an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area.

Patients include a biological system to which a treatment can be administered. A biological system can include, for example, an individual cell, a set of cells (e.g., a cell culture), an organ, or a tissue. Additionally, the term "patient" can refer to animals, including, without limitation, humans.

Treating or treatment of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

"Localized" delivery includes, delivery where one or more drugs are deposited within a tissue, for example, a nerve root of the nervous system or a region of the brain, or in close proximity (within about 10 cm, or preferably within about 5 cm, for example) thereto. "Targeted delivery system" provides delivery of one or more drugs depots in a quantity of pharmaceutical composition that can be deposited at the target site as needed for treatment of pain, inflammation or other disease or condition.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A drug delivery device for delivering a drug depot to a site beneath the skin of a patient, the drug delivery device comprising: a housing having a chamber configured to hold at least one drug depot, the chamber having a loading end and a delivery end, the loading end of the chamber having an opening for receiving a plunger and a drug depot and the delivery end having an opening for receiving the plunger and passage of the drug depot, the housing including a plurality of holes substantially perpendicular to the chamber and formed to at least partially intersect the chamber, at least one of the plurality of holes provided near the loading end and at least one of the plurality of holes provided near the delivery end; a capture pin configured to be receivable within each of the at least one of the plurality of holes provided near the loading end and the at least one of the plurality of holes provided near the delivery end to hold the drug pellet within the chamber, and a needle attached to the delivery end of the housing.

2. A drug delivery device for delivering a drug depot according to claim 1, wherein the drug depot comprises a drug pellet and the device and wherein the needle is detachable from the delivery end of the housing.

3. A drug delivery device according to claim 2, wherein movement of the plunger to an extended position moves the drug pellet within the chamber of the housing out the delivery end of the housing and out of the needle to the site beneath the skin.

4. A drug delivery device according to claim 2, wherein the capture pin is inserted into the at least one hole provided at the loading end and/or the delivery end, so that at least a portion of the capture pin protrudes into the chamber.

5. A drug delivery device according to claim 4, wherein the capture pin is configured to be deformable in at least a region where it protrudes into the chamber.

6. A drug delivery device according to claim 5, wherein the capture pin is configured to be deformable to allow the drug pellet to pass through the chamber when the plunger is inserted into the chamber and a force is applied to the plunger.

7. A drug delivery device according to claim 5, wherein the capture pin comprises a substantially cylindrical pin having an internal cavity.

8. A drug delivery device according to claim 5, wherein at least the region where the capture pin protrudes into the chamber comprises a tapered end.

9. A drug delivery device for delivering a drug pellet to a site beneath the skin of a patient, the drug delivery device comprising: a housing having a chamber configured to hold at least one drug pellet, the chamber having a loading end and a delivery end, the loading end of the chamber having an opening for receiving a plunger and a drug pellet and the delivery end having an opening for receiving the plunger and passage of the drug pellet, the housing including a first hole and a second hole, each hole being substantially perpendicular to the chamber and each formed to at least partially intersect the chamber, the first hole provided near the loading end and the second hole provided near the delivery end; a capture pin configured to be receivable within each of the first and second holes to hold the drug pellet within the chamber, wherein at least a portion of each inserted capture pin protrudes into the chamber; and a needle attached to the delivery end of the housing.

10. A drug delivery device for delivering a drug pellet according to claim 9, wherein the needle is detachable from the delivery end of the housing.

11. A drug delivery device for delivering a drug pellet according to claim 9, wherein movement of the plunger to an extended position moves the drug pellet within the chamber of the housing out the delivery end of the housing and out of the needle to the site beneath the skin.

12. A drug delivery device for delivering a drug pellet according to claim 9, wherein the capture pin is configured to be deformable in at least a region where it protrudes into the chamber.

13. A drug delivery device for delivering a drug pellet according to claim 9, wherein the capture pin is configured to be deformable to allow the drug pellet to pass through the chamber when the plunger is inserted into the chamber and a force is applied to the pin.

14. A drug delivery device for delivering a drug pellet according to claim 9, wherein the capture pin comprises a substantially cylindrical pin having a cavity.

15. A drug delivery device for delivering a drug pellet according to claim 9, wherein at least the region where the capture pin protrudes into the chamber comprises a tapered end.

16. A method of delivering a drug pellet to a site beneath the skin, the method comprising: providing a housing having a chamber configured to hold at least one drug pellet, the chamber having a loading end and a delivery end, the loading end of the chamber having an opening for receiving a plunger and a drug pellet and the delivery end having an opening for receiving the plunger and passage of the drug pellet, the housing including a distal hole and a proximal hole, each hole being substantially perpendicular to the chamber and each formed to at least partially intersect the chamber; inserting a capture pin within the distal hole; loading at least one drug pellet; inserting a capture pin within the proximal hole; inserting a cannula at the target site, the cannula having a proximal end and a distal end, the proximal end of the cannula having an opening to receive a drug pellet, the distal end of the cannula capable of insertion to the site beneath the skin of the patient and having an opening for passage of the drug pellet; and attaching the loaded housing to the proximal end of the cannula, wherein movement of the plunger to an extended position moves the drug pellet out of the distal end of the chamber and moves the pellet into the proximal end and distal end of the cannula to the site beneath the skin.

17. A method for delivering a drug pellet according to claim 16, wherein a portion of each inserted capture pin protrudes into the chamber, each capture pin configured to be deformable in at least a region where it protrudes into the chamber to allow the drug pellet to pass through the chamber when the plunger is inserted into the chamber and a force is applied to the plunger.

18. A method for delivering a drug pellet according to claim 16, wherein the capture pin comprises a substantially cylindrical pin having a cavity.

19. A method for delivering a drug pellet according to claim 17, wherein at least the region where the capture pin protrudes into the chamber comprises a tapered end.

* * * * *